United States Patent
Hansen et al.

(10) Patent No.: US 9,005,597 B2
(45) Date of Patent: Apr. 14, 2015

(54) FORMULATION FOR TREATMENT OF VAGINAL DRYNESS

(75) Inventors: Ketil Andre Hansen, Tonsberg (NO); Tore Fagerland, Nesoya (NO); John Afseth, Oslo (NO); Matthew Leigh, Muttenz (CH); Elsa Kung, Basel (SE); Peter van Hoogevest, Bubendorf (SE)

(73) Assignee: Medlite A/S, Holmestrand (NO)

( * ) Notice: Subject to any disclaimer, the term of this patent is extended or adjusted under 35 U.S.C. 154(b) by 316 days.

(21) Appl. No.: 12/998,393

(22) PCT Filed: Oct. 29, 2009

(86) PCT No.: PCT/EP2009/064312
§ 371 (c)(1),
(2), (4) Date: Jul. 7, 2011

(87) PCT Pub. No.: WO2010/049499
PCT Pub. Date: May 6, 2010

(65) Prior Publication Data
US 2011/0262381 A1    Oct. 27, 2011

Related U.S. Application Data

(60) Provisional application No. 61/197,799, filed on Oct. 30, 2008.

(51) Int. Cl.
| A61K 31/765 | (2006.01) |
| A61P 15/02  | (2006.01) |
| A61K 9/14   | (2006.01) |
| A61K 9/00   | (2006.01) |
| A61K 47/10  | (2006.01) |
| A61K 47/14  | (2006.01) |
| A61K 47/26  | (2006.01) |
| A61K 47/44  | (2006.01) |

(52) U.S. Cl.
CPC .............. *A61K 9/0034* (2013.01); *A61K 47/10* (2013.01); *A61K 47/14* (2013.01); *A61K 47/26* (2013.01); *A61K 47/44* (2013.01)

(58) Field of Classification Search
USPC ...................... 424/78.17, 486, 488
See application file for complete search history.

(56) References Cited

U.S. PATENT DOCUMENTS

| 5,726,164 A * | 3/1998 | Weder et al. ................. 514/80 |
| 6,248,363 B1 * | 6/2001 | Patel et al. ................. 424/497 |
| 6,805,874 B1 * | 10/2004 | Lutz et al. ................. 424/401 |
| 6,913,759 B2 | 7/2005 | Borgman et al. |
| 2003/0083314 A1 | 5/2003 | Yiv et al. |
| 2004/0151774 A1 * | 8/2004 | Pauletti et al. ............. 424/486 |
| 2005/0090557 A1 * | 4/2005 | Muhammad et al. ........ 514/627 |
| 2006/0018951 A1 | 1/2006 | Maniar et al. |
| 2007/0104783 A1 | 5/2007 | Domb et al. |
| 2009/0130029 A1 * | 5/2009 | Tamarkin et al. ............ 424/47 |

FOREIGN PATENT DOCUMENTS

| EP | 0 525 655 A1 | 2/1993 |
| WO | WO 03/050190 A2 | 6/2003 |
| WO | WO 2004/041118 A2 | 5/2004 |

OTHER PUBLICATIONS

International Search Report of the International Searching Authority; International Application No. PCT/EP2009/064312; International Filing Date: Oct. 29, 2009; Date of Mailing; Jan. 21, 2010; 3 Pages.
Written Opinion of the International Searching Authority; International Application No. PCT/EP2009/064312; International Filing Date; Oct. 29, 2009; Date of Mailing; Jan. 21, 2010; 5 Pages.
International Preliminary Report and Written Opinion of the International Searching Authority; International Application No. PCT/EP2009/064312; International Filing Date: Oct. 29, 2009; Date of Mailing; May 3, 2011; 6 Pages.

* cited by examiner

*Primary Examiner* — Ernst V Arnold
*Assistant Examiner* — Hong Yu
(74) *Attorney, Agent, or Firm* — Cantor Colburn LLP

(57) ABSTRACT

The present invention is directed to a composition for treating vaginal dryness and lack of lubrication comprising: a poloxamer component; a phospholipid component; an optional oil component; and a non-aqueous carrier; wherein the composition is substantially anhydrous. In another aspect, the present invention is directed to a method of treating vaginal dryness comprising the step of administering to a patient suffering from vaginal dryness the above composition.

23 Claims, No Drawings

FORMULATION FOR TREATMENT OF VAGINAL DRYNESS

BACKGROUND OF THE INVENTION

1. Field of the Invention

The invention relates generally to compositions and methods for vaginal treatments. Particularly it relates to substantially anhydrous semi-solid to solid compositions containing poloxamers. The composition forms coherent structured bilayer gel in a moist environment at or above body temperature, which unexpectedly provides long lasting and improved moisture and lubrication.

2. Description of the Related Art

Vaginal dryness is a common condition. It may affect women of all ages. The most common cause of vaginal dryness is decreased estrogen levels, which leads to thinning and drying of the vaginal wall. However, other factors such as medical conditions and psychological conditions including stress, depression and anxiety may also contribute to vaginal dryness. Vaginal dryness may make some daily activities uncomfortable, and it can also create quality of life issues for women and their partners.

Problems due to insufficient lubrication and dryness are generally addressed by vaginal compositions that provide or restore normal lubrication and hydration functions. These compositions are in the forms of creams, gels, films, liquids, solids and foams. However, most compositions suffer from the problems such as inconvenience and can be messy to use, irritating, and poor lasting quality. As such, it is appreciated that there is an unmet need for a lubricant that is non-irritating to both partners, easy and convenient to use, and provides long lasting moisture and lubricious properties.

Various types of natural and synthetic polymers have been generally employed in the compositions for vaginal treatments utilizing the polymer's muco adhesion and prolonging effects for topical applications. Where poloxamers are included, they are commonly used in combination with bioactive compounds or optionally used with other specific polymers wherein the specific polymers provide a more specialized role such as pH maintenance. The compositions disclosed in the prior art mostly contain water as the vehicle, which require preservatives to prevent spoilage and which has the limitation that the active ingredients should be insensitive to water.

Illustratively, U.S. Pat. No. 6,913,759 discloses an aqueous composition containing benzydamine hydrochloride, polyoxyalkylene block copolymer and propylene glycol. The composition has a pH value in the range of 3.5 to 7 and is allegedly effective in treating vaginal infections.

Other vaginal treatment compositions are also known. For example, U.S. Patent No. 2006/0018951 discloses a pH-responsive film comprising a biocompatible, hydrophilic polymer such as chitosan lactate, which is positively charged at a first pH and in an electronically neutral form at a higher pH; and an alkylene oxide polymer or copolymer including poloxamers. It is disclosed that the film may be used for contraception, treatment of vaginal infections, and enhancement of vaginal lubrication.

U.S. Patent No. 2007/0104783 discloses a bioadhesive sticker tablet containing one or more bioadhesive polymers including poloxamer. Even though the patent discloses that the composition may be applied to vaginal mucosa, it is mainly used for the treatment of ulcers or lesions in the oral cavity.

WO 2004/041118 discloses polymer foams and films for delivery of therapeutic agents to and through nasal, oral or vaginal mucosa. The foams and films contain a substrate polymer and a pharmacologically effective agent. The substrate polymer may be poloxamer. The patent does not disclose a composition that is in a solid to semi solid form at ambient temperature but transforms to a gel like structure at body temperature.

As such, it is appreciated that there is still a need for another composition containing poloxamer that is effective for treating vaginal dryness and has all the desired characters of a vaginal lubricant. The present invention is believed to be an answer to that need.

BRIEF SUMMARY OF THE INVENTION

In one aspect, the present invention is directed to a composition for treating vaginal dryness and lack of lubrication comprising:
(a) a poloxamer component;
(b) a phospholipid component;
(c) an optional oil component; and
(d) a non-aqueous carrier;
wherein the composition is substantially anhydrous.

In another aspect, the present invention is directed to a method of treating vaginal dryness comprising the step of administering to a patient suffering from vaginal dryness the above composition.

These and other aspects will become apparent upon reading the following detailed description and claims.

DETAILED DESCRIPTION OF THE INVENTION

It has been surprisingly found that by employing an appropriate combination of materials in suitable amounts, it is possible to produce a solid to semi solid composition for vaginal treatment that is user-friendly, non-irritating, and provides coherent stable gel above 30° C. The composition also has long lasting moisture and lubricious properties, is anhydrous and does not require preservatives which are frequently irritating.

Accordingly, the present invention is a composition for treating vaginal dryness and lack of lubrication comprising:
(a) a poloxamer component;
(b) a phospholipid component;
(c) an optional oil component; and
(d) a non-aqueous carrier;
wherein the composition is substantially anhydrous.

Each of these components is described in more detail below.

Poloxamer Component

Poloxamers are generic block copolymers composed of a hydrophobic polyoxypropylene backbone with twin hydrophilic poloxyethylene side chains to confer surfactant properties. Because the lengths of the backbone and the side chains can be customized, a variety of poloxamers exist; and they have different properties.

In one embodiment of the invention, poloxamers used in the compositions of the invention have molecular weights ranging from about 2000 to 15,000, preferably between 7000 and 9000. Although liquid poloxamers such as poloxamer 124 may be considered, generally solid poloxamers, preferably ones with melting points between about 50° C. and 60° C. are used to provide the desired properties of the composition.

The lengths of the polyoxypropylene backbone and polyoxyethylene chains reflect the hydrophilic/lipophilic balance of surfactants, commonly known as HLB value. In one embodiment, the HLB values of the poloxamers used are in the range between 12 to 24, preferably between 20 and 24. Examples of the suitable poloxamer include poloxamer 124, poloxamer 188, poloxamer 237, poloxamer 335 and combinations thereof.

The amount of poloxamer component included in the composition of the invention preferably ranges from about 15 to about 45 wt %, more preferably from about 20 to 40 wt %, and most preferably from about 25 to 35 wt %, all weight percents being based on the total weight of the composition.

Phospholipid Component

Phospholipids are generally known as lecithins which are widely used functional ingredients in food products, essentially as surfactants and viscosity modifiers. As such, the lecithins are commercial grades of natural phospholipids which are obtained chiefly from soya beans and other plant sources by deoiling and purifying by means of solvent extraction. Lecithins comprise primarily of phospholipids which are the natural building blocks for cells found in all living organisms.

Phospholipid molecules are amphiphilic due to a hydrophilic head which may be choline, inositol, ethanolamine molecule, attached to twin lipophilic hydrocarbon tails linked by a glycerol molecule. The hydrocarbon chain of phospholipids may comprise between 14 to 18 carbon atoms and may be fully or partially saturated thereby conferring different phase transition temperatures. Due to this unique configuration, phospholipids have the tendency to arrange and organize in the form of bilayer at various temperatures depending on their phase transition temperature which provide the structural and functional basis of all cell walls and membranes.

Phospholipids are widely used in drug delivery as liposomes to carry active compounds within the bilayer arrangement. For the purpose of the present invention, it is preferred to use pure grade and fractionated grades phospholipids which comprise phosphatidylcholine, phosphatidyl ethanolamine, phosphatidyl serine, phosphatidyl inositol, the mono acryl equivalents, and non polar lipids, wherein the phosphatidylcholine is present in an amount of at least about 30% based on the total weight of the phospholipid composition.

The amount of phospholipid component included in the composition of the invention preferably ranges from about 2 to about 20 wt %, more preferably from about 2.5 to 10 wt %, and most preferably from about 4 to 7 wt %, all weight percents being based on the total weight of the composition.

Oil Component

The oil component is an optional ingredient in the composition of the invention. Examples of the oils useful in the composition of the invention include, but are not limited to, mono, di and tri glycerides, fatty acid esters, ethers of fatty alcohols consisting of 12 to 20 carbon atoms, and mixtures thereof. One preferred triglyceride is cocoglyceride, which has been found to provide desirable emollient and lubricity. Oils may be present in an amount of from about 5 to about 40% based on the total weight of the composition.

Non-Aqueous Carrier Component

Examples of suitable non-aqueous carriers that may be used in the composition and treatments of the invention include the following polyols: natural sugars, sucrose, sorbitol, mannitol, xylitol and synthetic dihydric alcohols such as propylene glycol, glycerol. In a preferred embodiment, the polyol is sorbitol. Preferably, the non-aqueous carrier component comprises from 30 to about 70% by weight, based on the total weight of the composition.

Additional Optional ingredients

Additional ingredients may also be optionally added to the composition of the invention. An anti-pruritic agent may optionally be used in the compositions of the invention to relieve irritation. In a preferred embodiment, the anti-pruritic agent is lauromacrogol. Other components that may be used optionally in the composition of the present invention include but are not limited to therapeutically active or beneficial compounds and excipients commonly used in topical compositions such as gelling or viscosity agents, preservatives and anti oxidants. The active or beneficial compound may be an anti microbial agent, an anti infective agent, hormone, enzymes, or physiological process regulating compound such as pH modifiers. Examples of suitable pH modifiers are lactic acid, glacial acetic acid, adipic acid, glutamic acid, HCl, phosphoric acid and buffers. Exemplary gelling agents include natural gums, acacia, xanthan, tragacanth, and hydrocolloids such as starch, carboxy methyl cellulose, hydroxylpropyl methyl cellulose, methacrylate polymers, polyvinyl pyrrolidone. Exemplary antioxidants include ascorbic acid or palmitate, tocopherols, butylated hydroxyl anisole, butylated hydroxyl toluene.

The amount of the additional optional ingredients preferably ranges to up to about 10 wt %, based on the total weight of the composition. In one exemplary embodiment, the additional optional ingredient is lauromacrogol at an amount preferably ranging from 2.5 wt % to about 10 wt %, and more preferably from about 4 wt % to 7 wt %, based on the total weight of the composition.

As used herein, the term "substantially anhydrous" refers to compositions which contain up to about 30% by weight of water which is bound to the polyol such as sorbitol or a polyhydric alcohol rather than water which is added freely as a vehicle.

The composition is in a solid to semi-solid form at room temperature; but it hydrates and forms coherent stable gel in moist environments at or above 30° C. or body temperature (about 37° C.). These properties unexpectedly provide long lasing moisture binding and improved lubricity for vaginal treatment. As used herein, the term "semi-solid" refers to a coherent waxy mass. The composition of the invention may be in any semi-solid to solid anhydrous form, for example, pessaries, suppositories, liquid filled soft gelatin capsules, and the like.

While not wishing to be bound by any particular theory, the poloxamer component and the phospholipid component are believed to act synergistically to carry other components of the composition, such as polyols in coherent structures. The composition takes the form of anhydrous semi-solid to solid at temperatures below 30° C. and gel like structure above 30° C. or body temperature for vaginal administration. Facilitated by the presence of phospholipids, the gel like structure is a coherent bilayered structure. It is stable under body temperatures for an extended period of time, thus effective for long lasting moisture and lubrication.

The compositions according to the invention advantageously may not require preservation for extended storage due to the composition being sufficiently anhydrous for microbes not to survive.

The compositions according to the present invention can be manufactured by conventional methods such as mixing, melting and congealing, compaction, molding or extruding. For example, for a particular composition, the components with desired amounts can be mixed at an elevated temperature then cooled down to a product in a solid or semi-solid form.

The composition of the invention is useful in treating vaginal dryness and lacking of lubrication. Accordingly, the present invention also encompasses a method of administering to the user's vagina the compositions of the present invention. The amount of the composition of the present invention applied to the affected area is generally an effective amount, wherein "effective amount" is whatever amount effectively treats dryness and/or lack of lubrication. In one embodiment, the composition of the invention is applied once or twice daily, depending on the severity of the condition. In one exemplary embodiment, each application should include between 500 mg and 5 g of the solid formulation in a single dose, and preferably between 1 g to 3 g in a single dose.

EXAMPLES

Example 1

Composition 1 was generally prepared as follows: the phospholipid was pre-dispersed in the sorbitol solution to form a gel, the poloxamer and cocoglyceride were then added to form a mixture, the mixture was stirred and heated at a temperature between 55° C.-60° C. until a smooth paste was formed. The molten composition was stirred, cooled to 45-50° C. and transferred to moulds or cooled further to a pliable mass which may be compacted or extruded as a solid composition. The detailed information of the composition is provided in Table 1.

Examples 2-7

Compositions 2-7 were prepared according to the general procedure provided in Example 1. The weight percentage of each component of compositions 2 to 7 are provided in Table 1.

TABLE 1

| | Composition (wt % content) | | | | | | |
|---|---|---|---|---|---|---|---|
| Component | 1 | 2 | 3 | 4 | 5 | 6 | 7 |
| Poloxamer 188 | 34 | 34 | 34 | 20 | 40 | 34 | 34 |
| Phospholipid | 5 | 5 | 5 | 7.5 | 7.5 | 5 | 5 |
| Cocoglycerides | 20 | 20 | 20 | 0 | 0 | 20 | 20 |
| Sorbitol Solution | 41 | 38 | 35 | 68.5 | 49.5 | 37.5 | 36-37.5 |
| Lauromacrogol | | 3 | 6 | 3 | 3 | 3 | 3 |
| Carboopol 974 P | | | | | | 0.5 | |
| Lactic Acid | | | | | | | 0.5-2.0 |

Preparation and Evaluation of Composition 2

To prepare the composition of Example 2, phospholipid is slowly added to the sorbitol solution in a 100 mL beaker and gradually stirred until all the phospholipid is uniformly dispersed. A magnetic stirrer may be used for slow stirring. For larger batches, mechanical mixers may be used. The lauromacrogol, cocoglyceride and poloxamer 188 are individually weighed into the beaker containing the phospholipid-sorbitol dispersion. The mixture is gently heated to about 60° C. with continuous gentle stirring to avoid aeration, until a homogeneous slurry is obtained. The mixture is then cooled to 45-50° C. by maintaining constant stirring and while still fluid, poured into nominal 3 g ovule pessary moulds. 2 g of the liquid-mixture at 45-50° C. is filled in each mould. The pessaries are left to set at room temperature for at least 1 hour before removing the solid waxy composition from the moulds. The final products are opaque cream-coloured waxy pessaries. As will be appreciated by one of skill in the art, the batch size produced in this example was 20 g, however, the method is suitable for scale up to larger batches by using larger stirring and heating equipment commensurate to the size of vessel.

The prepared pessary containing Composition 2 as produced above was given to a 40 year old pre-menopausal woman who has no previous experience with a vaginal long-lasting moisturizing product. The woman was asked to use Composition 2 (a suppository of 500 mg of formulation 2) and give a personal evaluation of the product.

The summary of the comments on the personal evaluation are as follows. The product was easy to administer, and the product dissolved completely and relatively quickly. The product had no feeling of volume and left no residual, no odor, and no color. Moisture was judged as very good, and the effects of the product were judged as rapid. The subject's vagina was very moist 13 hours after insertion, and still moist 17 hours and 72 hours after insertion of the product. The Examples show that the compositions according to the present invention have the desired features such as long-lasting lubrication effect, easy and convenient to use, and are quick to spread.

What is claimed is:

1. A composition for treating vaginal dryness and lack of lubrication comprising:
    (a) 15-45 wt % of a poloxamer component;
    (b) 2-20 wt % of a phospholipid component;
    (c) 0-40 wt % of an oil component;
    (d) 30-70 wt % of a non-aqueous carrier; and
    (e) 2.5-10 wt % of lauromacrogol;
    wherein all weight percents are based on the total weight of said composition, wherein the non-aqueous carrier comprises polyol, and wherein said composition is substantially anhydrous and contains up to about 30% by weight of water bound to the polyol.

2. The composition of claim 1, wherein said poloxamer component comprises from 20 to about 40% by weight, based on the total weight of the composition.

3. The composition of claim 1, wherein said poloxamer component comprises from 25 to about 35% by weight, based on the total weight of the composition.

4. The composition of claim 1, wherein said poloxamer component has a molecular weight ranging from about 2000 to about 15,000.

5. The composition of claim 1, wherein said poloxamer component has a molecular weight ranging from about 7000 to about 9000.

6. The composition of claim 1 wherein said poloxamer component has a melting point between about 50° C. and 60° C.

7. The composition of claim 1 wherein the poloxamer component is selected from the group consisting of poloxamer 124, poloxamer 188, poloxamer 237, poloxamer 335, and combinations thereof.

8. The composition of claim 1, wherein said phospholipid component comprises from 2.5 to about 10% by weight, based on the total weight of said composition.

9. The composition of claim 1, wherein said phospholipid component comprises from 4 to about 7% by weight, based on the total weight of said composition.

10. The composition of claim 1, wherein said phospholipid is selected from the group consisting of phosphatidylcholine, phosphatidyl ethanolamine, phosphatidyl serine, phosphatidyl inositol, non-polar lipids, the mono acyl equivalents thereof, and combinations thereof.

11. The composition of claim 10, wherein said phosphatidylcholine is present in an amount of about 30% based on the total weight of the phospho lipid.

12. The composition of claim 1, wherein said oil component comprises from 5 to about 40% by weight, based on the total weight of the composition.

13. The composition of claim 1, wherein said oil component is selected from the group consisting of mono, di- and tri-glycerides, fatty acid esters, ethers of fatty alcohols having 12 to 20 carbon atoms, and combinations thereof.

14. The composition of claim 13, wherein said oil component is cocoglyceride.

15. The composition of claim 1, wherein said polyol is selected from the group consisting of natural sugars, sucrose, sorbitol, mannitol, xylitol and synthetic dihydric alcohols such as propylene glycol, glycerol.

16. The composition of claim 15, wherein said polyol is sorbitol or a sorbitol solution.

17. The composition of claim 1, wherein said composition is in a solid to semi-solid form at room temperature.

18. The composition of claim 1, wherein said composition hydrates and forms coherent stable gel in moist environment at or above 30° C. or body temperatures.

19. The composition of claim 1, further comprising one or more additional ingredients selected from the group consisting of gelling agents, viscosity agents, preservatives, antioxidants, anti microbial agents, antiinfective agents, hormones, enzymes, and pH modifiers.

20. The composition of claim 19, wherein said gelling agent is selected from the group consisting of gelling agents are natural gums, acacia, xanthan, tragacanth, starch, carboxy methyl cellulose, hydroxyl propyl methyl cellulose, methacrylate polymers, polyvinyl pyrrolidone, and combinations thereof.

21. The composition of claim 19, wherein said antioxidant is selected from the group consisting of ascorbic acid, palmitate, tocopherols, butylated hydroxyl anisole, butylated hydroxyl toluene, and combinations thereof.

22. The composition of claim 19, wherein said pH modifier is selected from the group consisting of lactic acid, acetic acid, adipic acid, glutamic acid, HCl, phosphoric acid, buffers, and combinations thereof.

23. The composition of claim 19, wherein said additional ingredients comprise up to about 10% by weight, based on the total weight of said composition.

* * * * *